United States Patent
Klinder et al.

(10) Patent No.: US 10,045,754 B2
(45) Date of Patent: Aug. 14, 2018

(54) THREE DIMENSIONAL (3D) PRE-SCAN BASED VOLUMETRIC IMAGE DATA PROCESSING

(71) Applicant: KONINKLIJKE PHILIPS N.V., Eindhoven (NL)

(72) Inventors: Tobias Klinder, Uelzen (DE); Cristian Lorenz, Hamburg (DE); Martin Bergtholdt, Hamburg (DE); Rafael Wiemker, Kisdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 96 days.

(21) Appl. No.: 15/102,554

(22) PCT Filed: Nov. 25, 2014

(86) PCT No.: PCT/IB2014/066302
§ 371 (c)(1),
(2) Date: Jun. 8, 2016

(87) PCT Pub. No.: WO2015/087185
PCT Pub. Date: Jun. 18, 2015

(65) Prior Publication Data
US 2016/0310090 A1    Oct. 27, 2016

Related U.S. Application Data

(60) Provisional application No. 61/914,450, filed on Dec. 11, 2013.

(51) Int. Cl.
*A61B 6/00* (2006.01)
*A61B 5/055* (2006.01)
(Continued)

(52) U.S. Cl.
CPC .............. *A61B 6/488* (2013.01); *A61B 5/055* (2013.01); *A61B 6/03* (2013.01); *A61B 6/50* (2013.01);
(Continued)

(58) Field of Classification Search
CPC combination set(s) only.
See application file for complete search history.

(56) References Cited

U.S. PATENT DOCUMENTS 7,627,158 B2 * 12/2009  Hay ........................ G06K 9/32
                                                                382/131
7,957,572 B2 *  6/2011  Von Berg ................ G06T 7/149
                                                                345/419
(Continued)

FOREIGN PATENT DOCUMENTS

DE    102011083647    3/2013
EP          2017785    1/2009
(Continued)

OTHER PUBLICATIONS

Kortesniemi, et al., "To develop and evaluate automatic image registration for organ dose calculation in CT", Acta Radiol 2012.

*Primary Examiner* — Anand Bhatnagar

(57) ABSTRACT

A method includes determining a registration transform between first three dimensional pre-scan image data and second three dimensional pre-scan image data based on a predetermined registration algorithm. The method further includes registering first volumetric scan image data and second volumetric scan image data based on the registration transform. The method further includes generating registered image data. A system (100) includes a pre-scan registerer (122) that determines a registration transform between first three dimensional pre-scan image data and second three dimensional pre-scan image data based on a predetermined registration algorithm. The system further
(Continued)

includes a volume registerer (126) that registers first volumetric scan image data and second volumetric scan image data based on the registration transform, generating registered image data.

27 Claims, 11 Drawing Sheets

(51) Int. Cl.
*G06T 3/40* (2006.01)
*G06T 5/00* (2006.01)
*G06T 7/00* (2017.01)
*G06T 7/30* (2017.01)
*G06T 7/37* (2017.01)
*G06T 7/11* (2017.01)
*A61B 6/03* (2006.01)
*G01R 33/54* (2006.01)

(52) U.S. Cl.
CPC .......... *A61B 6/5235* (2013.01); *A61B 6/5264* (2013.01); *A61B 6/5288* (2013.01); *G06T 3/4038* (2013.01); *G06T 5/003* (2013.01); *G06T 7/0014* (2013.01); *G06T 7/11* (2017.01); *G06T 7/30* (2017.01); *G06T 7/37* (2017.01); *A61B 6/032* (2013.01); *A61B 6/037* (2013.01); *A61B 6/541* (2013.01); *G01R 33/543* (2013.01); *G06T 2207/10072* (2013.01); *G06T 2207/10081* (2013.01); *G06T 2207/20201* (2013.01); *G06T 2207/20221* (2013.01)

(56) References Cited

U.S. PATENT DOCUMENTS

| | | | | |
|---|---|---|---|---|
| 8,094,900 | B2* | 1/2012 | Steines | G01R 33/56 382/128 |
| 8,317,705 | B2* | 11/2012 | Stapf | A61B 5/416 382/128 |
| 2004/0204644 | A1* | 10/2004 | Tsougarakis | G01R 33/56 600/410 |
| 2005/0065421 | A1* | 3/2005 | Burckhardt | A61B 6/032 600/407 |
| 2007/0160312 | A1* | 7/2007 | Blaffert | G06T 7/30 382/294 |
| 2009/0080746 | A1* | 3/2009 | Xu | A61B 5/055 382/131 |
| 2010/0129005 | A1* | 5/2010 | Tao | G01R 33/4833 382/291 |
| 2010/0220909 | A1 | 9/2010 | Thielemans | |
| 2011/0255760 | A1 | 10/2011 | Mahesh | |
| 2012/0082350 | A1 | 4/2012 | Wollenweber | |
| 2013/0039555 | A1* | 2/2013 | Xu | G06T 7/0038 382/131 |
| 2013/0094742 | A1* | 4/2013 | Feilkas | A61B 6/584 382/131 |
| 2013/0137968 | A1* | 5/2013 | Reisman | G01R 33/56563 600/415 |
| 2015/0332464 | A1* | 11/2015 | O'Keefe | G06K 9/00201 348/47 |

FOREIGN PATENT DOCUMENTS

| | | |
|---|---|---|
| WO | 2012/075577 | 6/2012 |
| WO | 2012/153219 | 11/2012 |

* cited by examiner

THREE DIMENSIONAL (3D) PRE-SCAN BASED VOLUMETRIC IMAGE DATA PROCESSING

CROSS REFERENCE TO RELATED APPLICATIONS

This application is the U.S. National Phase application under 35 U.S.C. § 371 of International Application No. PCT/IB2014/066302, filed Nov. 25, 2014, published as WO 2015/087185 on Jun. 18, 2015, which claims the benefit of U.S. Provisional Patent Application No. 61/914,450 filed Dec. 11, 2013. These applications are hereby incorporated by reference herein.

The following generally relates to imaging and more particularly to processing volumetric image data based on three dimensional (3D) pre-scan image data, and is described with particular application to computed tomography (CT). However, the following is also amenable to other imaging modalities.

A CT scanner includes an x-ray tube that emits radiation that traverses an examination region and an object therein. A detector array located opposite the examination region across from the x-ray tube detects radiation that traverses the examination region and the object therein and generates projection data indicative of the examination region and the object therein. A reconstructor processes the projection data and reconstructs volumetric image data indicative of the examination region and the object therein.

The volumetric image data can be processed to generate images. The registration of images between two scans can be important for visual or automatic comparison of the images, e.g., to highlight changes associated with a tumor follow up scan. Generally, image registration is the alignment of two (or more) images. Fast and robust alignment are needed for the clinical environment. Unfortunately, fast and robust alignment is, in many cases, difficult to achieve, especially if the images have little overlapping content.

Organ displacement and deformation (e.g., due to respiratory, cardiac, etc. motion) can affect registration, as well as image-guided applications and image acquisition. Motion models that contain prior information of the motion of interest have been proposed to reduce the uncertainty caused by the motion. Motion models have been learned from four dimensional image data, e.g., 4D-CT. If the data is from the same subject, the model will be subject-specific. Otherwise, the motion model will be general or generic to the subject.

A subject specific motion model typically outperforms general motion models due the subject-specific breathing patterns. Unfortunately subject-specific models require additional 4D data, which may change the clinical workflow and add dose to the subject. A general-motion model does not require the additional 4D acquisition and can be individualized. However, if no subject specific motion information is available, then, unfortunately, the individualization to a particular patient is limited.

Image segmentation is another task in medical image analysis. Image segmentation algorithms based on a growing process may not be suitable for smaller volumes. As an example, a scan performed to measure airway wall thickness to rule out chronic obstructive pulmonary disease (COPD) typically includes scanning only a small sub-portion of the lungs about the airway wall. With such limited data, it may be difficult to distinguish airways from lung parenchyma. Even when a target organ is fully covered, it still may be difficult to segment the target organ. For example, where the boundary between two organs is unclear, the segmentation may not be able to accurately delineate the two organs.

Aspects described herein address the above-referenced problems and others.

This following describes an approach for registering volumetric image data with a registration transform generated based on three dimensional (3D) pre-scan image data. The registration can be improved by extending the volumetric image data with a sub-portion of the 3D pre-scan image data such that the extended volumetric image data includes more overlapping content relative to the initial, non-extended volumetric image data.

In one aspect, a method includes determining a registration transform between first three dimensional pre-scan image data and second three dimensional pre-scan image data based on a predetermined registration algorithm. The method further includes registering first volumetric scan image data and second volumetric scan image data based on the registration transform. The method further includes generating registered image data.

In another aspect, a system includes a pre-scan registerer that determines a registration transform between first three dimensional pre-scan image data and second three dimensional pre-scan image data based on a predetermined registration algorithm. The system further includes a volume registerer that registers first volumetric scan image data and second volumetric scan image data based on the registration transform, generating registered image data.

In another aspect, a method includes combining 3D pre-scan image data with volumetric image data from a volume scan. The 3D pre-scan image data was used to plan the volume scan, generating combined image data. The method further includes segmenting tissue of interest from the volumetric image data based on the combined image data.

In another aspect, a system includes a combiner that combines 3D pre-scan image data with volumetric image data from a volume scan. The 3D pre-scan image data was used to plan the volume scan, generating combined image data. The system further includes a segmentor that segments tissue of interest from the volumetric image data based on the combined image data.

The invention may take form in various components and arrangements of components, and in various steps and arrangements of steps. The drawings are only for purposes of illustrating the preferred embodiments and are not to be construed as limiting the invention.

FIG. 1 schematically illustrates an imaging system in connection with a pre-scan registerer, a volume/pre-scan registerer, a volume registerer, and a combiner and segmentor.

Figures 18, 19:
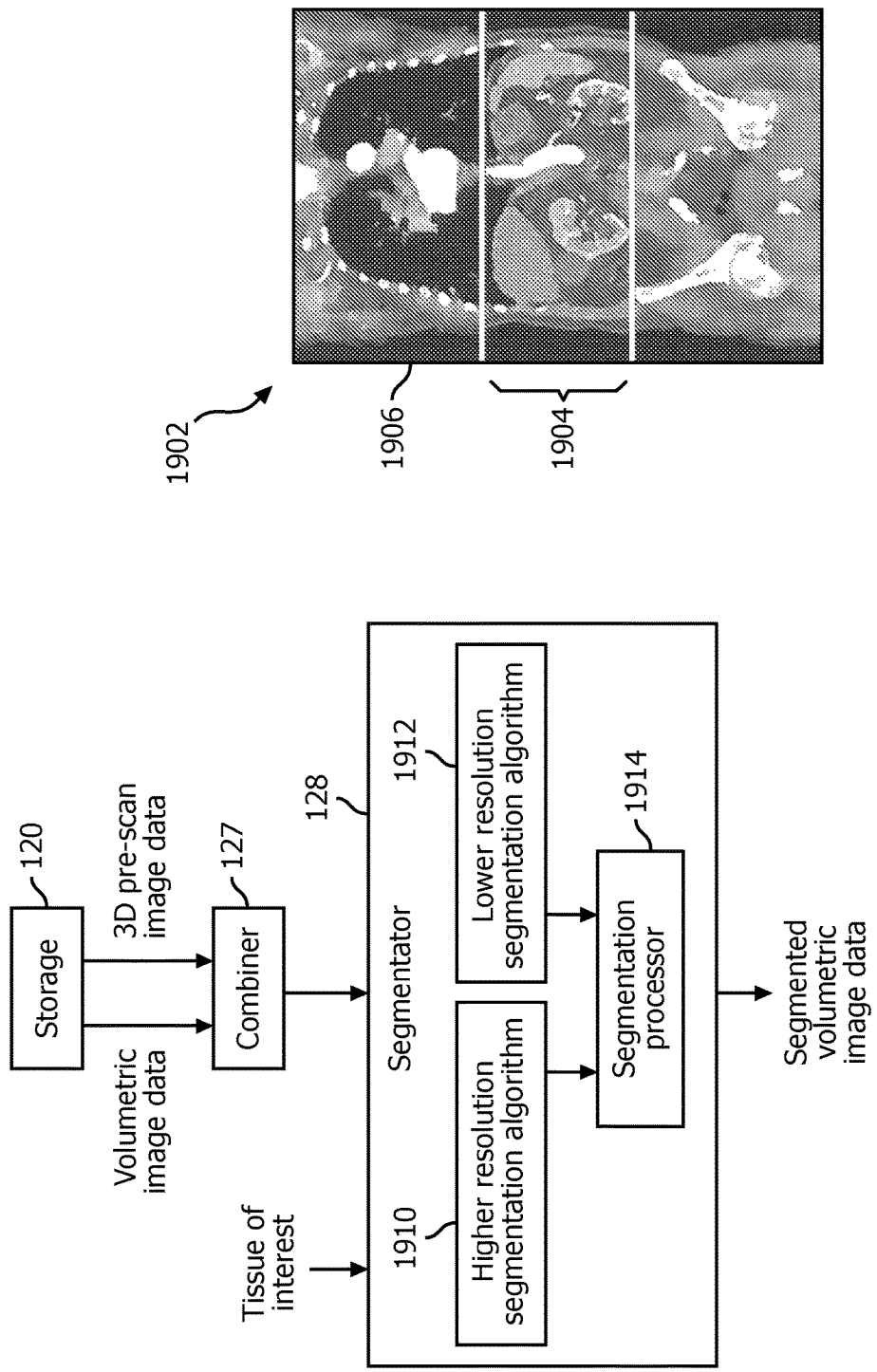

FIG. 18 schematically illustrates an example of the segmentor in connection with the storage 120 and the combiner.

FIG. 19 illustrates combined image data, including 3D pre-scan image data combined with volumetric image data.

Figure 20:
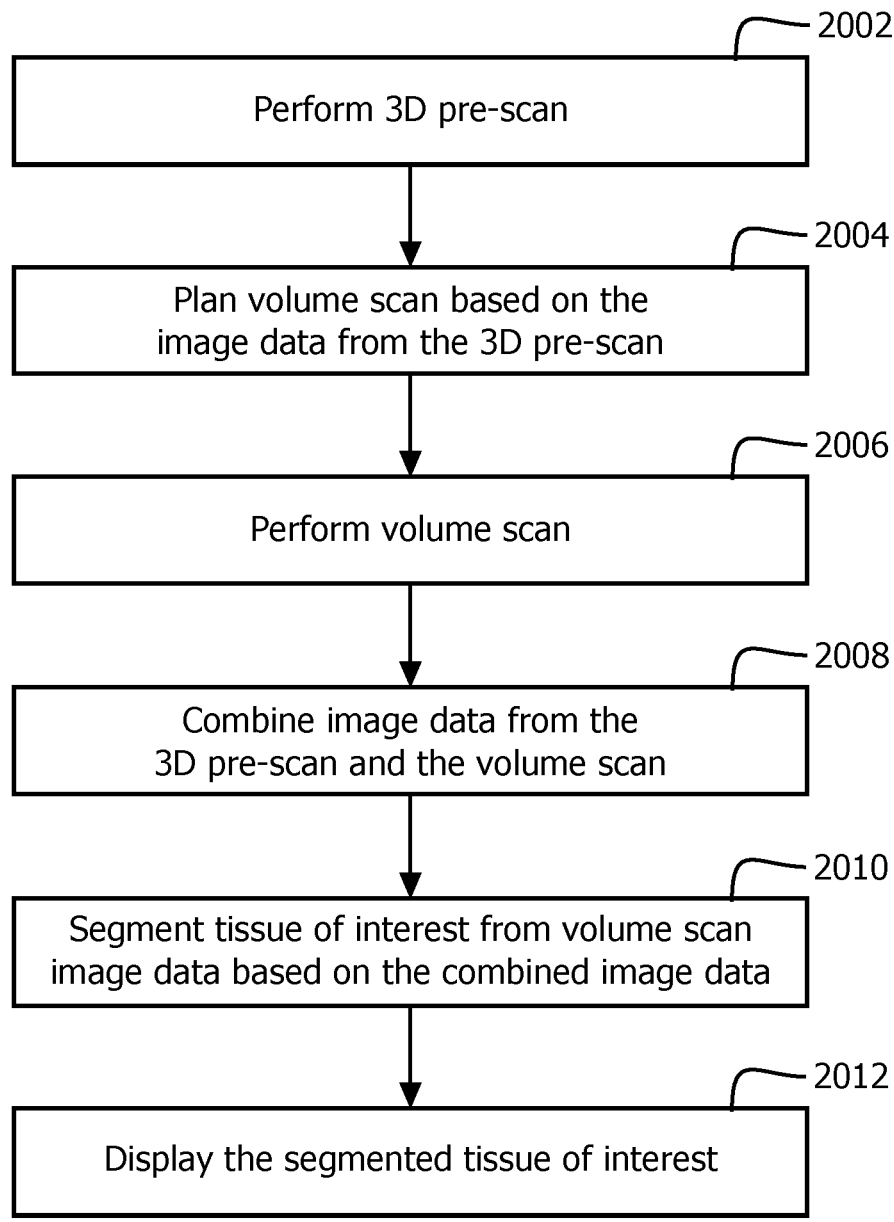

FIG. 20 illustrates a method for segmenting a region of interest from volumetric image data.

Figure 1:
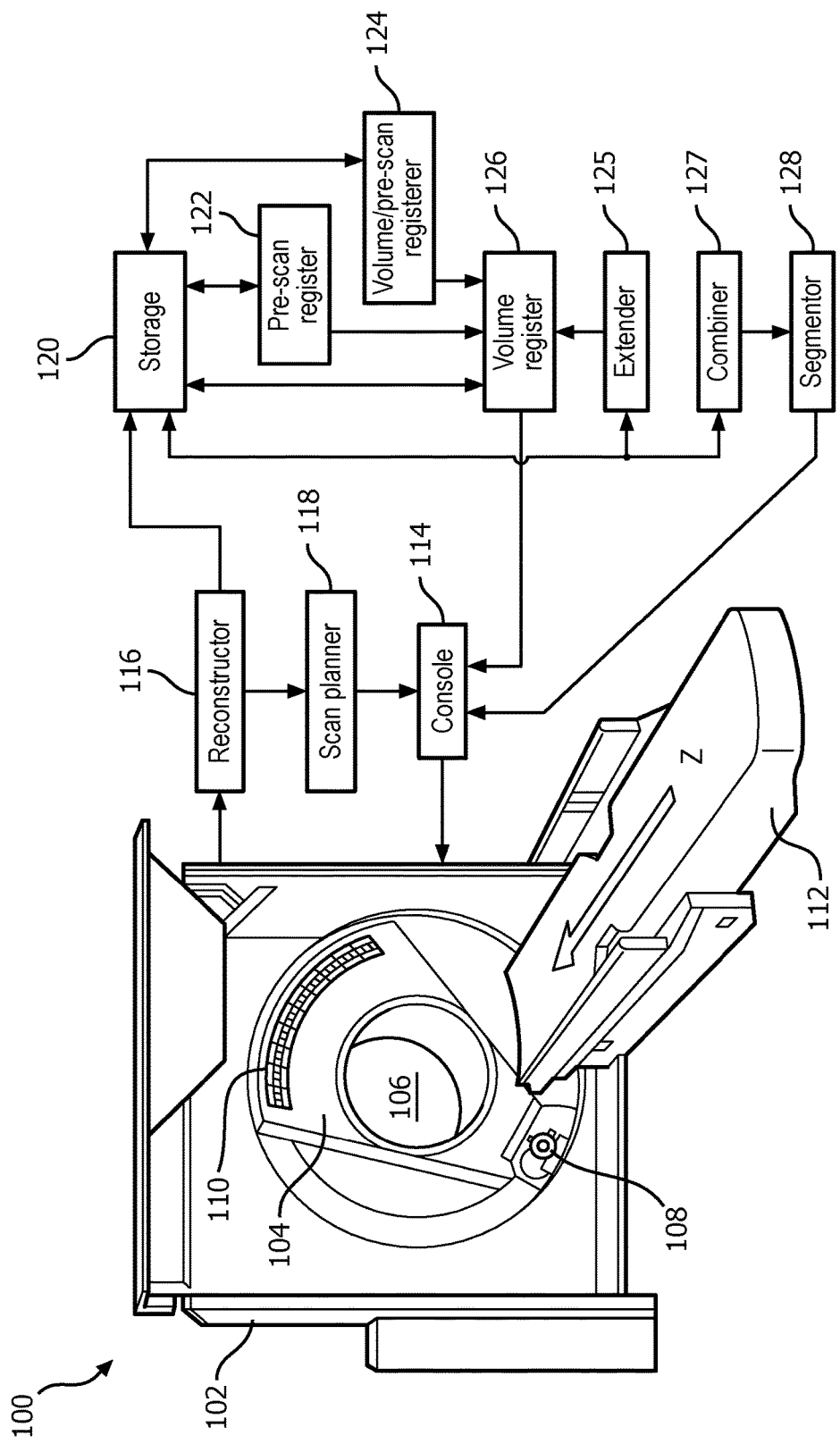

FIG. 1 illustrates an imaging system 100 such as a computed tomography (CT) scanner. The illustrated imaging system 100 includes a stationary gantry 102 and a rotating gantry 104, which is rotatably supported by the stationary gantry 102. The rotating gantry 104 rotates around an examination region 106 about a longitudinal or z-axis. A radiation source 108, such as an x-ray tube, is supported by the rotating gantry 104 and rotates with the rotating gantry 104 about the examination region 106, and emits radiation that traverses the examination region 106.

A radiation sensitive detector array 110 is located opposite the radiation source 108 across the examination region 106. The radiation sensitive detector array 110 detects radiation traversing the examination region 106 and generates a signal indicative thereof. A support 112 supports an object or subject in the examination region 106. A computer serves as an operator console 114 and includes an output device such as a display and an input device such as a keyboard, mouse, etc. Software resident on the console 114 allows the operator to control an operation of the system 100 such as data acquisition.

Figure 2:
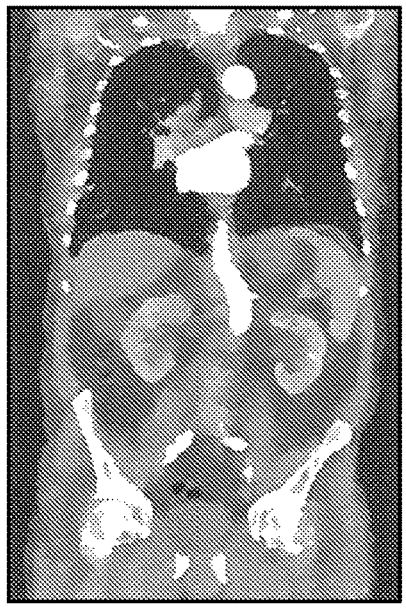
FIG. 2 illustrates a coronal plane of lower dose, non-diagnostic image quality image data.
Figure 3:
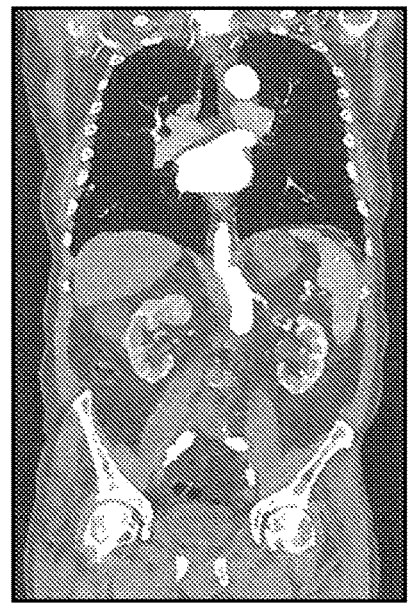
FIG. 3 illustrates a coronal plane of diagnostic image quality image data for the same field of view of FIG. 2.

Examples of suitable data acquisition include two-dimensional (2D) and/or three-dimensional (3D) pre-scans and include volumetric scans. An example of a 2D pre-scan is a 2D scout (also referred to as pilot or surview) scan. Generally, this type of pre-scan is a 2D projection image, similar to an x-ray. An example of a 3D pre-scan is a lower dose volumetric scan, which, generally, is not used for diagnostic purposes due to the lower image quality (e.g., lower contrast resolution). An example of lower dose image data is shown in FIG. 2. FIG. 3 shows a diagnostic image data with higher contrast resolution and covering the same field of view for image quality comparison.

An example of the volumetric scan is a helical or spiral scan with scan setting (e.g., electrical current and voltage, pitch, slice thickness, etc.), which result in an image quality at which the image data can be used for diagnostic purposes. Again, FIG. 3 shows an example of such image data. Another example of the volumetric scan is a perfusion scan in which the radiation source 108 and the scanned object/subject remain at a constant location with respect to each other and a scan of the same volume of the object or subject is repeatedly scanned over multiple revolutions or rotations of the rotating gantry 104.

Returning to FIG. 1, a reconstructor 116 reconstructs the signal generated by the radiation sensitive detector array. For example, the reconstructor 116 can reconstruct a pre-scan image data for a pre-scan scan or data acquisition and volumetric image data for a volumetric scan or data acquisition. The pre-scan image data can be a 2D projection and/or 3D lower dose image data, as discussed herein. The reconstructor 116 employs corresponding algorithms for reconstructing 2D projections and 3D lower dose/lower image quality image data, and volumetric (diagnostic image quality) image data, and/or other reconstruction algorithms.

A scan planner 118 plans a volumetric scan based on pre-scan image data. The volumetric scan plan is generated using the pre-scan image data to identify at least a start position of the volumetric scan. The pre-scan image data can also be used to identify a stop location or a length of the volumetric scan, which can be used to derive a stop location. The start and end locations define a field of view (or an extent at least along the z-axis). The field of view represents the sub-portion of the object or subject that will be scanned or reconstructed during the volumetric scan. The volumetric scan plan is provided to the console 114, which starts and stops data acquisition according to the volumetric scan plan.

The sub-portion of the object or subject that is scanned may or may not include moving structure. For instance, with a subject, the scan may entail scanning a region that includes the lungs, which include periodically moving structure, or scanning a leg, which does not include periodically moving structure. In the former instance, performing the pre-scan and performing the volume scan with the moving structure in approximately the same motion state may facilitate ensuring that tissue of interest identified in the pre-scan data for scanning is covered in volumetric scan. However, the pre-scan and the volume scan can be performed during different motion states, as described in greater detail below.

Storage 120, in the illustrated embodiment, stores 2D and/or 3D pre-scan image data and volumetric scan reconstructed image data. This includes reconstructed image data for two or more data acquisitions such as a data acquisition and a follow up data acquisition, including a pre-scan and a volumetric scan for each of the data acquisitions. For example, a subsequent volumetric scan may be performed after a volumetric scan to generate comparative image data for tissue of interest such as a tumor, a lesion, etc. The multiple data acquisitions can be used to determine whether a tumor has decreased, increased or remained the same in size.

A pre-scan registerer 122 registers two or more sets of 3D pre-scan image data, generating a registration transformation therebetween. The registration can be between, for example, a first set of image data and a second subsequently acquired set of image data, for example, in connection with a follow-up scan. In the illustrated embodiment, the pre-scan registerer 122 determines the registration transform based on a predetermined registration algorithm. The predetermined registration algorithm may include a rigid and/or elastic registration algorithm.

Generally, the registration transform transforms the different sets of image data into a single coordinate system. This includes using one of the two sets of 3D pre-scan image data as a reference image data set and determining a registration transform that transforms the other of the two sets of 3D pre-scan image data set to the coordinate system of the reference image data set. Where there are more than two sets of 3D pre-scan image data, two or more registration transforms can be determined. Furthermore, two or more of the registration transforms can be generated based on a same reference image data set or different reference image data sets.

Figure 4:
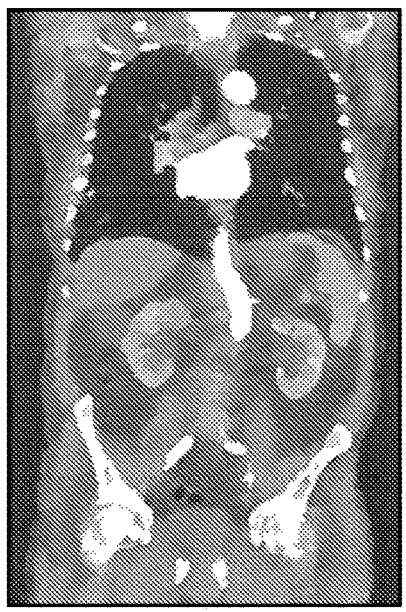
FIG. 4 illustrates a coronal plane of three dimensional pre-scan image data.
Figure 5:
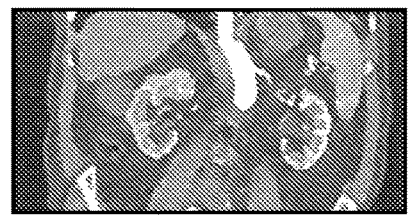
FIG. 5 illustrates a coronal plane of diagnostic scan image data acquired from a scan plan based on the three dimensional pre-scan image data of FIG. 4 and having a smaller field of view relative to FIG. 4.

A volume/pre scan registerer 124 registers 3D pre-scan and volumetric image data, generating a registration transformation therebetween. From above, the field of view (or the z-axis extent) of the volumetric scan is smaller than the field of view of the corresponding 3D pre-scan image data. An example is shown in FIGS. 4 and 5. FIG. 4 represents a coronal view of image data from a 3D pre-scan, and FIG. 5 represents a coronal view of image data from a corresponding volumetric scan. From FIGS. 4 and 5, the field of view of the volumetric scan image data is a sub-set of the field of view of the 3D pre-scan image data. As described in greater detail below, the registration transformation can be used to compensate for subject motion.

A volume registerer 126 registers two sets of the volumetric image data based on the registration transform determined by the pre-scan registerer 122 and/or the registration transform determined by the volume/pre scan registerer 124. Because the scanned field of view is greater for the pre-scan image data relative to the volumetric image data, the registration transform between the two sets of 3D pre-scan image data, using the registration transform determined by the pre-scan registerer 122, generally, may result in an improved initialization and/or more accurate registration of the two sets of the volumetric image data relative to a configuration in which the volume registerer 126 registers the two sets of the volumetric image data without using this registration transform.

An extender 125 extends volumetric image data sets that will be registered. As described in greater detail below, in one instance, the extender extends, prior to registration, the volumetric image data sets with the pre-scan image data sets. This may include extending the volumetric image data sets to be registered so that the volumetric image data sets have approximately the same FOV. In another instance, one or more of the volumetric image data sets to be registered are extended, but the resulting volumetric image data sets do not have the same FOV.

A combiner 127 combines 3D pre-scan and volumetric image data, generating combined data. A segmentor 128 segment tissue of interest based on the combined data. As described in greater detail below, in one instance, the combined data, relative to the volumetric image data alone, may provide an image data set with additional context for the organ of interest, e.g., where only a sub-portion of the organ of interest is represented in the volume scan and/or one or more organs neighboring the organ of interest is not represented in the volume scan.

In the illustrated embodiment, at least one of the registration transform for the multiple sets of 3D pre-scan data, the registration transform for the 3D pre-scan and volumetric image data, or the segmentation is stored in the storage 120. In another embodiment, the at least one of the registration transform for the multiple sets of 3D pre-scan data, the registration transform for the 3D pre-scan and volumetric image data, or the segmentation can be stored in other storage.

Furthermore, in the illustrated embodiment, the at least one of the registration transform for the multiple sets of 3D pre-scan data, the registration transform for the 3D pre-scan and volumetric image data, or the segmentation can be conveyed to and displayed via the console 114. In another embodiment, the at least one of the registration transform for the multiple sets of 3D pre-scan data, the registration transform for the 3D pre-scan and volumetric image data, or the segmentation are displayed through a display monitor or the like of another device (e.g., a computer, smartphone, etc.) and/or a stand-alone display.

The pre-scan registerer 122, the volume/pre scan registerer 124, the combiner 127, and/or the segmentor 128 can be implemented via one or more computer processors (e.g., a central processing unit (CPU), a microprocessor, a controller, etc.) executing one or more computer executable instructions embedded or encoded on computer readable storage medium, which excludes transitory medium, such as physical memory. However, at least one of the computer executable instructions can alternatively be carried by a carrier wave, signal, and other transitory medium and implemented via the one or more computer processors.

In another embodiment, one or more of the pre-scan registerer 122, the volume/pre scan registerer 124, the combiner 127, the volume registerer 126, or the segmentor 128 is omitted.

Figure 6:
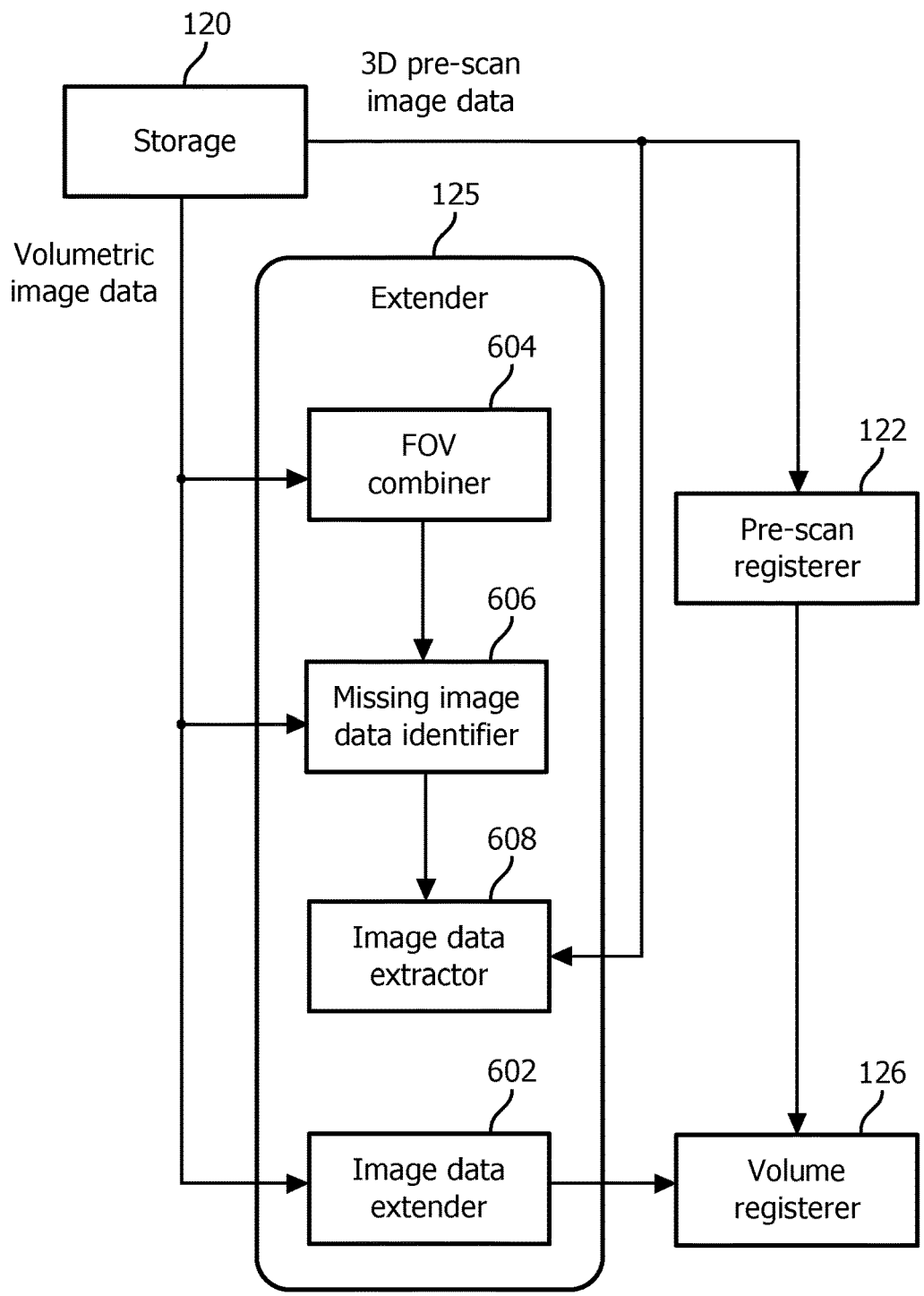
FIG. 6 illustrates an example of the extender of FIG. 1.
Figure 7:
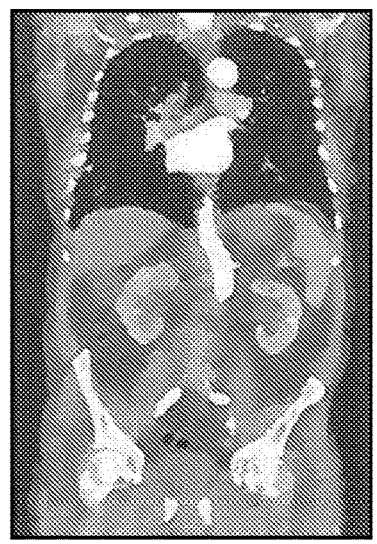
FIG. 7 illustrates first pre-scan image data.
Figure 8:
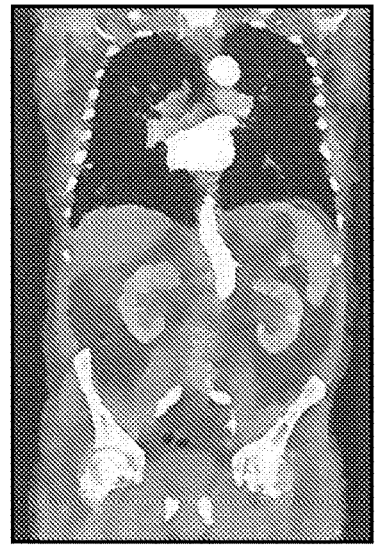
FIG. 8 illustrates second pre-scan image data.
Figure 9:
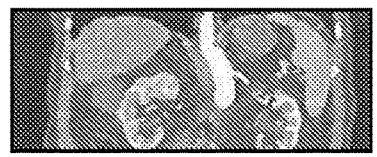
FIG. 9 illustrates first volumetric image data acquired from a scan plan generated based on the first pre-scan image data.
Figure 10:
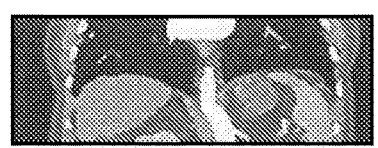
FIG. 10 illustrates second volumetric image data acquired from a scan plan generated based on the second pre-scan image data.

FIG. 6 illustrates an example of the extender 125 of FIG. 1. The extender 125, as briefly discussed above extends, prior to registration, the volumetric image data that will be registered, using the pre-scan image data. FIGS. 7 and 8 respectively show pre-scan 3D image data for first and second 3D pre-scans, and FIGS. 9 and 10 respectively show volumetric image data for the first and second volumetric scans. Returning to FIG. 6, the volumetric scans are conveyed to a field of view (FOV) combiner 604, which combines the first and second volumetric image data (e.g., FIGS. 9 and 10) to determine a combined field of view.

A missing image data identifier 606 identifies a sub-portion of the combined field of view that is not part of the first and second volumetric image data, for each of the first and second volumetric image data. An image data extractor 608 extract image data corresponding to the identified missing image data from the 3D pre-scan image data. An image data extender 602 extends the first volumetric image data with the image data extracted from the first pre-scan image data and extends the second volumetric image data with the image data extracted from the second pre-scan image data. The resulting extended first and second volumetric image data have approximately a same field of view.

Figure 11:
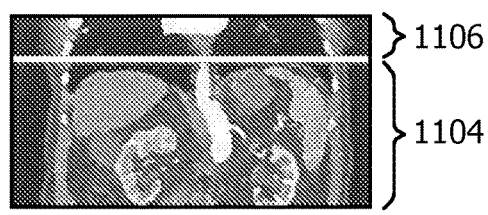
FIG. 11 illustrates first extended volumetric image data, which includes the first volumetric image data of FIG. 9 extended with a sub-portion of the first pre-scan image data of FIG. 7.
Figure 12:
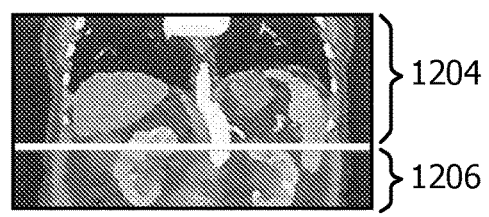
FIG. 12 illustrates second extended volumetric image data, which includes the second volumetric image data of FIG. 10 extended with a sub-portion of the second pre-scan image data of FIG. 8.

FIGS. 11 and 12 respectively show extended first volumetric image data and extended second volumetric image data. In FIG. 11, a first portion of the image data 1104 includes the first volumetric image data and a second portion of the image data 1106 includes the first extracted portion added thereto. In FIG. 12, a first portion of the image data 1204 includes the second volumetric image data and a second portion of the image data 1206 includes the second extracted portion added thereto. The extended first volumetric image data and the extended second volumetric image data are conveyed to the volume registerer 126, which register the extended first and second image data. In the illustrated embodiment, the extended first and second image data are registered using the registration transformation generated by the pre-scan registerer 122, as described herein.

In a variation, the extended first and second image data are registered without the registration transformation generated by the pre-scan registerer 122. The registration of the first and second volumetric data, in one instance, is more accurate when the extended first volumetric image data and the extended second volumetric image data are registered relative to registering the first and second volumetric data without extending the first and second volumetric data. For example, where there is little overlap between the first and second volumetric data, the extended first and second volumetric image data provides additional image data and cover the same volume of data, which artificially increases the overlap, providing further image data for the registration. In a variation, the extended first volumetric image data and the second volumetric image data are not registered. Rather, the extended first volumetric image data and the second volumetric image data can be displayed, conveyed to another component, otherwise processed, etc.

Figure 13:
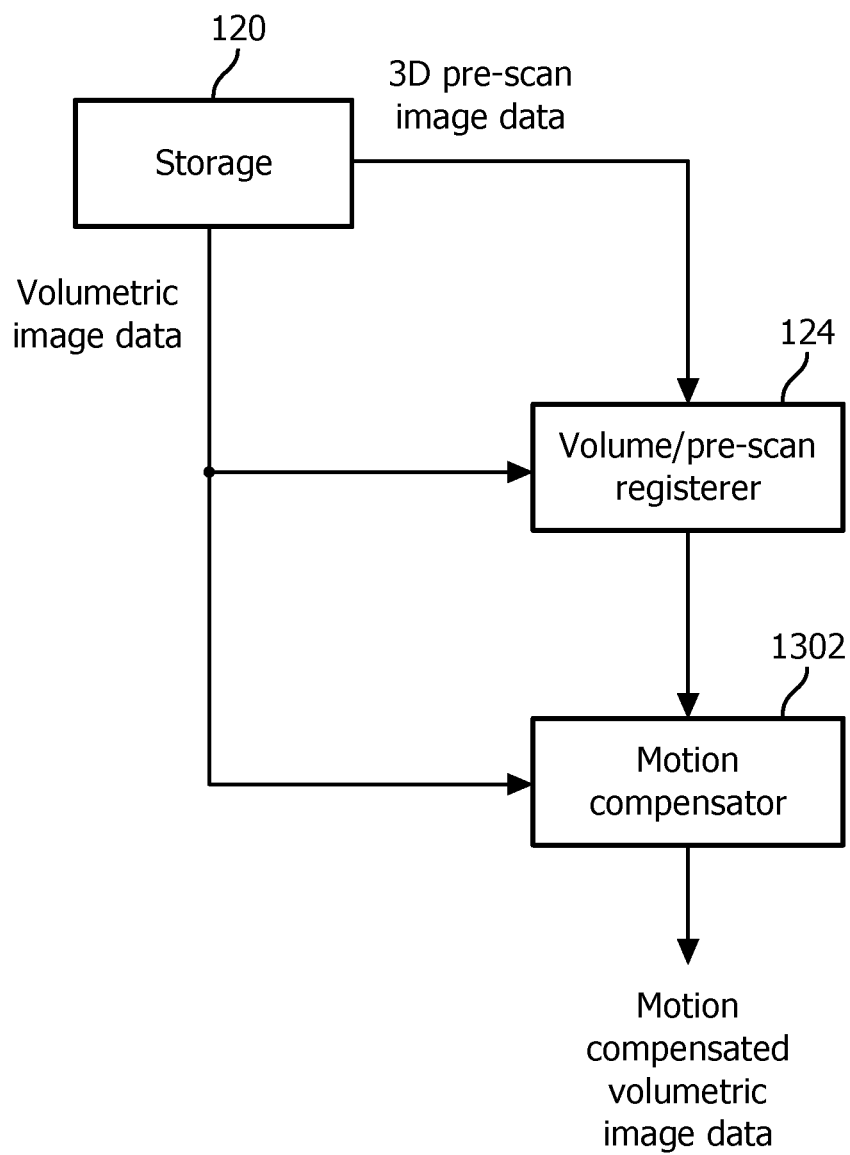
FIG. 13 illustrates a variation of FIG. 1 that includes a motion compensator.

As briefly discussed above, the registration transformation determined by the volume/pre scan registerer 124 can be utilized to compensate for motion. FIG. 13 schematically illustrates an embodiment in which the registration transformation determined by the volume/pre scan registerer 124 is utilized to compensate for motion.

With this embodiment, the 3D pre-scan image data and the volumetric image data are acquired during different motion states. For example, one of the scans can be performed during full inspiration while the other is performed during full expiration. An intermediate motion state may alternatively be used. Furthermore, the motion may alternatively be cardiac and/or other motion.

The registration transformation provides a motion vector field (MVF). A patient specific model can be extracted from the MVF. By linearly scaling the patient specific motion model, organ locations at different motion phases can be predicted. With respect to respiratory motion, the corresponding phase information could come from a spirometer, a marker block placed on the subject, etc. The above approach does not require acquiring additional data or changing the current workflow. Alternatively, or additionally, data can be obtained from the 3D pre-scan image data and the volumetric image data, and used to improve a general model.

A motion compensator 1302 compensates the first and second volumetric image data based on the respective motion vectors. The motion compensated first volumetric image data and the motion compensated second volumetric image data are conveyed to the volume registerer 126, which registers the image data, as described herein. In an alternative embodiment, the motion state information could come from a spirometer, a respiratory belt, a marker placed on the abdomen of the subject, etc. For cardiac motion, the motion state information could come from an electrocardiogram (ECG) signal.

Figure 14:
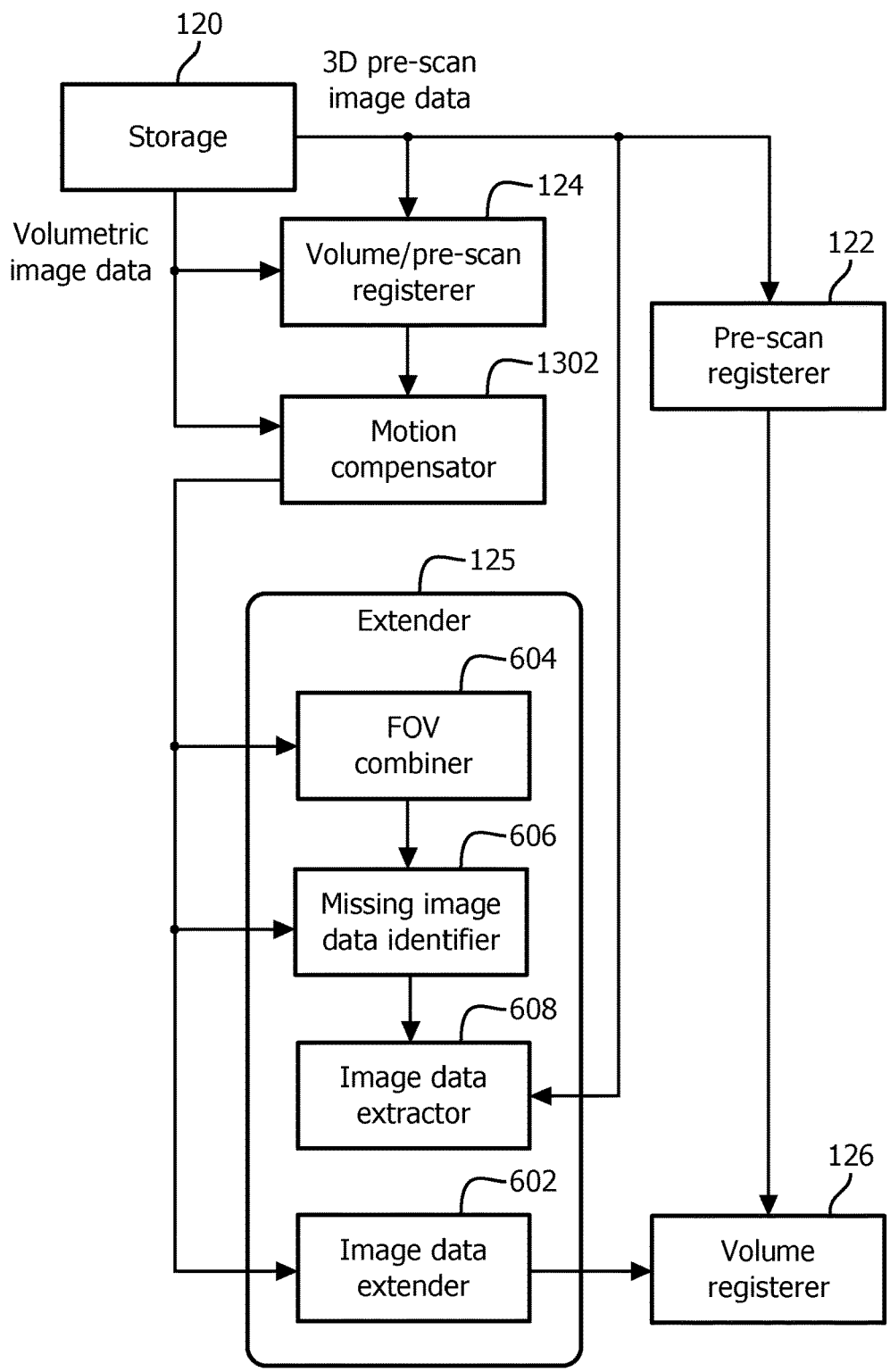
FIG. 14 illustrates a variation which includes a combination of FIGS. 6 and 13.

In yet another variation, shown in FIG. 14, the system 100 motion compensates (e.g., as discussed in connection with FIG. 13) and extends (e.g., as discussed in connection with FIG. 6) the volumetric image data. In FIG. 14, the volumetric image data is first motion compensated and then extended. In a variation, the volumetric image data is first extended and then motion compensated. In the latter variation, the motion compensation can be over the entire extended volumetric image data, just the original volumetric image data, and/or a sub-portion of the extended volumetric image data.

Although the above has been discussed in connection with multiple sets of CT image data, it is to be appreciated that one or more of the sets of the data can be positron emission tomography (PET) data, single photon emission tomography (SPECT) data, magnetic resonance imaging (MM) data, and/or other image data.

Figure 15:
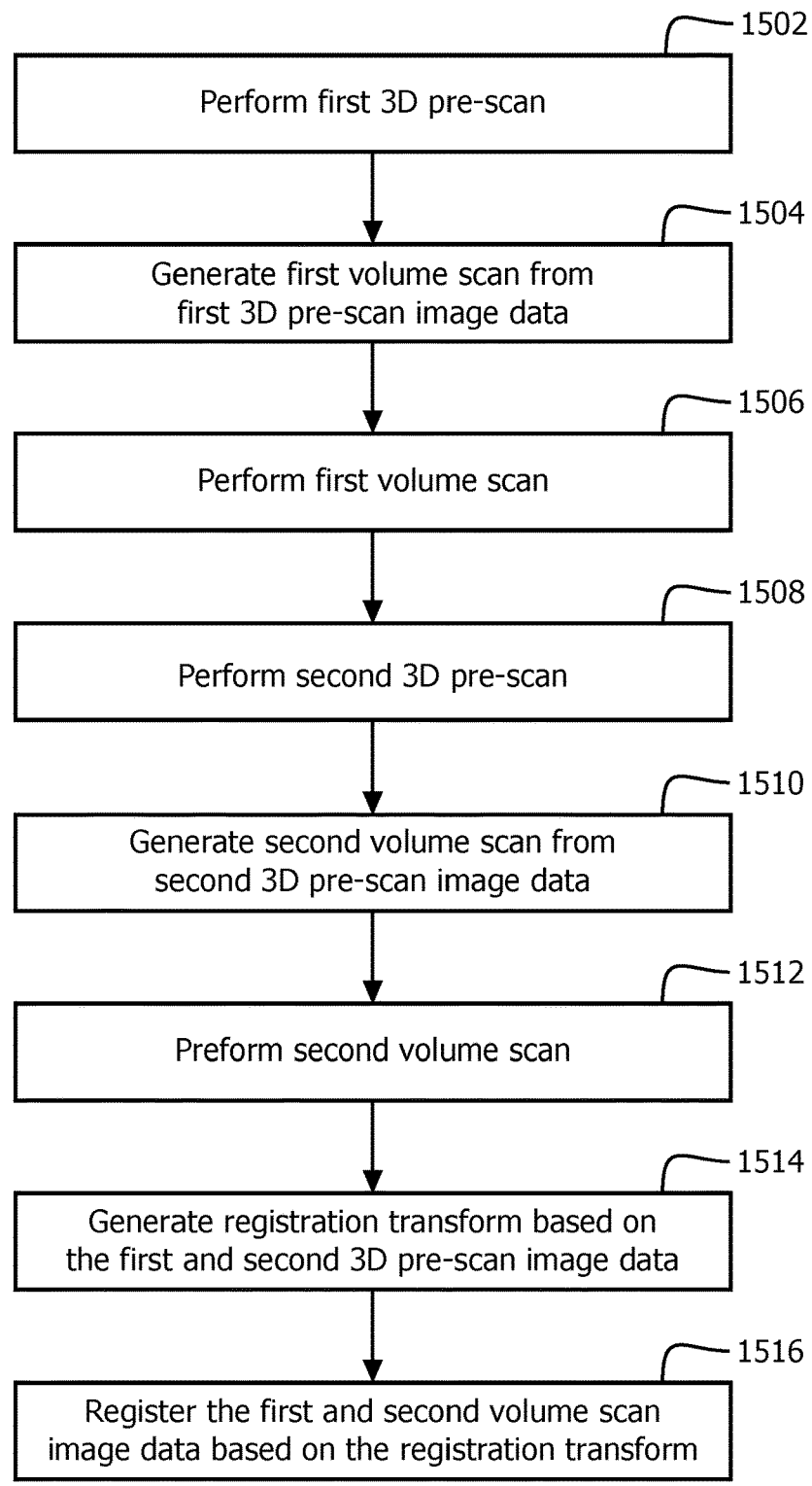
FIG. 15 illustrates a method for registering images from different volumetric image data sets using a registration transform created from a registration of 3D pre-scan data corresponding to the different volumetric image data sets.

FIG. 15 illustrates a method for registering images from different image data sets using a registration transform created from a registration of 3D pre-scan data corresponding to the different image data sets.

It is to be appreciated that the ordering of the acts of these methods is not limiting. As such, other orderings are contemplated herein. In addition, one or more acts may be omitted and/or one or more additional acts may be included.

At 1502, a first 3D pre-scan is performed, generating first 3D pre-scan image data.

At 1504, a first volume scan plan is generated based on the first 3D pre-scan image data.

At 1506, a first volume scan is performed based on the first volume scan plan, generating first volumetric image data.

At 1508, a second 3D pre-scan is performed, generating second 3D pre-scan image data.

At 1510, a second volume scan plan is generated based on the second 3D pre-scan image data.

At 1512, a second volume scan is performed based on the second volume scan plan, generating second volumetric image data.

At 1514, a registration transform is generated based on the first and the second 3D pre-scan image data.

At 1516, the first volumetric image data and the second volumetric image data are registered using the registration transform.

The above acts may be implemented by way of computer readable instructions, encoded or embedded on computer readable storage medium, which, when executed by a computer processor cause the processor to carry out the described acts. Additionally or alternatively, at least one of the computer readable instructions is carried by a signal, carrier wave and other transitory medium and implemented by the computer processor.

Figure 16:
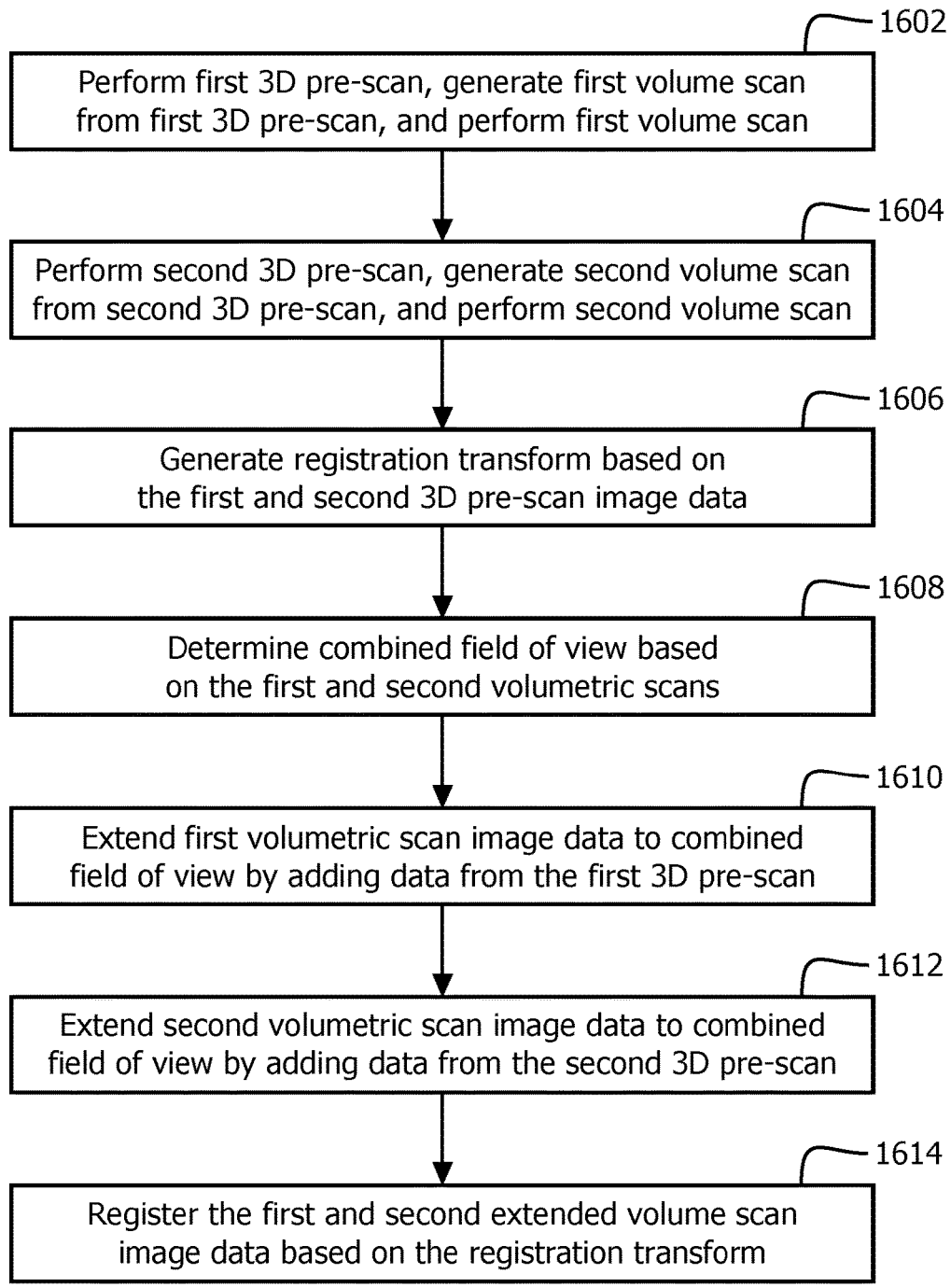
FIG. 16 illustrates a variation of FIG. 15 that includes extending the different volumetric image data sets to cover a combined field of view of both of the different volumetric image data sets.

FIG. 16 illustrates a variation of FIG. 15 that includes extending the different image data sets to cover the combined field of view of both of the different image data sets.

It is to be appreciated that the ordering of the acts of these methods is not limiting. As such, other orderings are contemplated herein. In addition, one or more acts may be omitted and/or one or more additional acts may be included.

At 1602, a first 3D pre-scan is performed, generating first 3D pre-scan image data, a first volume scan plan is generated based on the first 3D pre-scan image data, and a first volume scan is performed based on the first volume scan plan, generating first volumetric image data.

At 1604, a second 3D pre-scan is performed, generating second 3D pre-scan image data, a second volume scan plan is generated based on the second 3D pre-scan image data, and a second volume scan is performed based on the second volume scan plan, generating second volumetric image data.

At 1606, a registration transform is generated based on the first and the second 3D pre-scan image data.

At 1608, a combined field of view is determined based on a first field of view of the first volumetric image data and a second field of view of the second volumetric image data.

At 1610, the first volumetric image data is extended to the combined field of view by adding data from the first 3D pre-scan image data, creating first extended volumetric image data.

At 1612, the second volumetric image data is extended to the combined field of view by adding data from the second 3D pre-scan image data, creating second extended volumetric image data.

At 1614, the first extended volumetric image data and the second extended volumetric image data are registered using the registration transform.

In a variation, act 1606 is omitted, and the first extended volumetric image data and the second extended volumetric image data are registered without the registration transform generated based on the first and the second 3D pre-scan image data.

The above acts may be implemented by way of computer readable instructions, encoded or embedded on computer readable storage medium, which, when executed by a computer processor cause the processor to carry out the described acts. Additionally or alternatively, at least one of the computer readable instructions is carried by a signal, carrier wave and other transitory medium and implemented by the computer processor.

Figure 17:
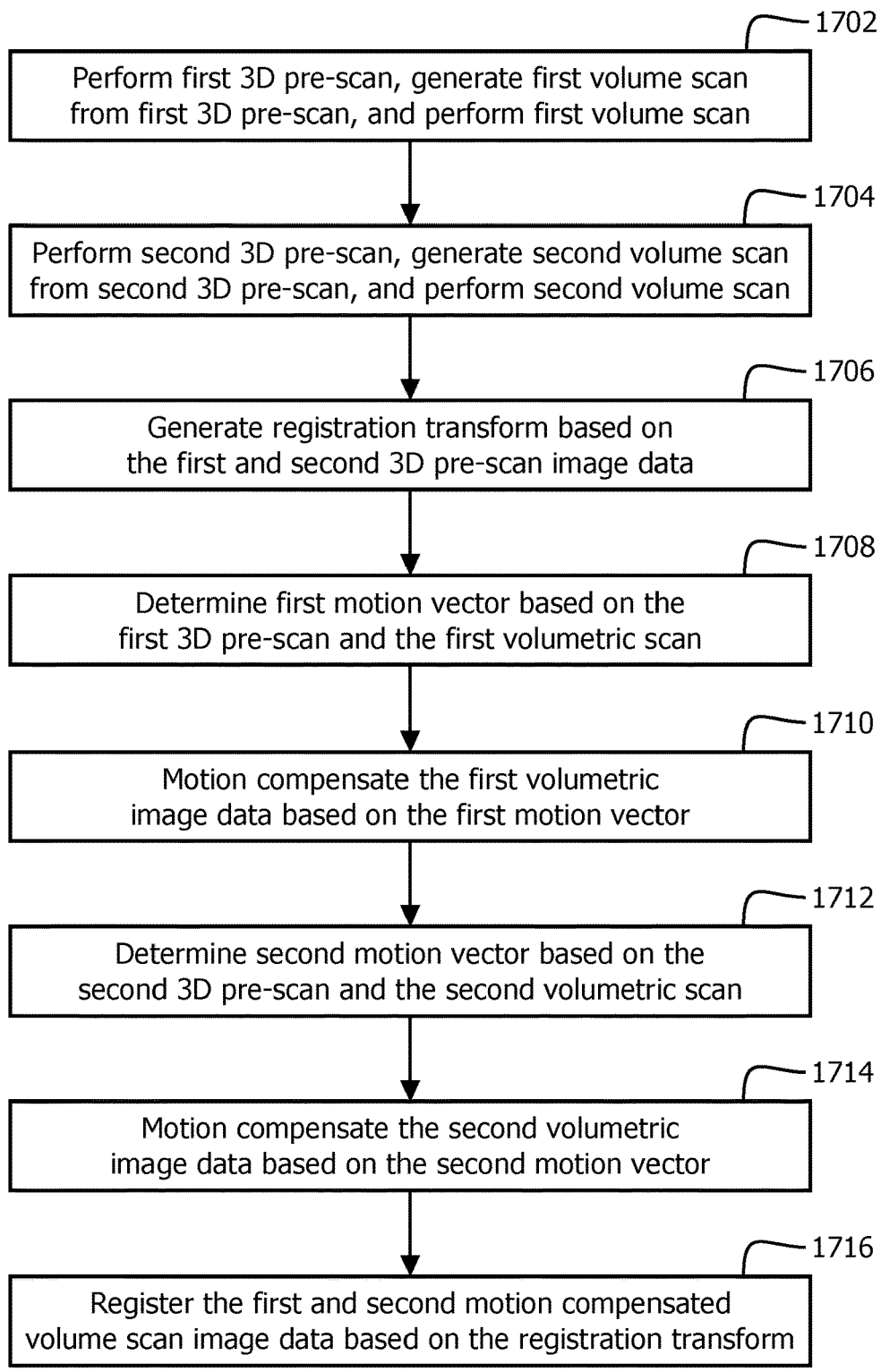
FIG. 17 illustrates a variation of FIG. 15 that includes motion compensating each of the different volumetric image data sets based on a motion vector field derived from the 3D pre-scan data and the different volumetric image data sets.

FIG. 17 illustrates a variation of FIG. 15 that includes motion compensating each of the different image data sets based on a motion vector field derived from the 3D pre-scan data and the different image data sets.

It is to be appreciated that the ordering of the acts of these methods is not limiting. As such, other orderings are contemplated herein. In addition, one or more acts may be omitted and/or one or more additional acts may be included.

At 1702, a first 3D pre-scan is performed, generating first 3D pre-scan image data, a first volume scan plan is generated based on the first 3D pre-scan image data, and a first volume scan is performed based on the first volume scan plan, generating first volumetric image data.

At 1704, a second 3D pre-scan is performed, generating second 3D pre-scan image data, a second volume scan plan is generated based on the second 3D pre-scan image data, and a second volume scan is performed based on the second volume scan plan, generating second volumetric image data.

At 1706, a registration transform is generated based on the first and the second 3D pre-scan image data.

At 1708, a first motion vector field is generated based on the first 3D pre-scan image data and the first volumetric image data.

At 1710, the first volumetric image data is motion compensated based on the first motion vector, creating motion compensated first volumetric image data.

At 1712, a second motion vector field is generated based on the second 3D pre-scan image data and the second volumetric image data.

At 1714, the second volumetric image data is motion compensated based on the second motion vector, creating motion compensated second volumetric image data.

At 1716, the first motion compensated volumetric image data and the second motion compensated volumetric image data are registered using the registration transform.

The above acts may be implemented by way of computer readable instructions, encoded or embedded on computer readable storage medium, which, when executed by a computer processor cause the processor to carry out the described acts. Additionally or alternatively, at least one of the computer readable instructions is carried by a signal, carrier wave and other transitory medium and implemented by the computer processor.

FIG. 18 schematically illustrates an example of the segmentor 128 in connection with the storage 120 and the combiner 127. In this example, the combiner 127 obtains volumetric image data and 3D pre-scan image data from the storage 120. In other examples, the combiner 127 may obtain the volumetric image data and/or the 3D pre-scan image data from another device, for example, the reconstructor 116 (FIG. 1), other reconstructor, and/or other device.

The 3D pre-scan image data is the pre-scan data used to plan the volume scan that produced the volumetric image data. As described herein, generally, the field of view (along the z-axis extent) of the volumetric scan is smaller than the field of view of the corresponding 3D pre-scan image data. Also, as described at least in connection with FIGS. 2-5, an image contrast resolution of the 3D pre-scan image data is lower than the image contrast resolution of the volumetric image data.

Both, generally, are due to the pre-scan being performed to plan the volume scan, and the larger field of view and/or the lower dose limits the dose deposited to the subject. Different resolution image data is shown in FIGS. 4 and 5, where FIG. 4 represents a coronal view of lower resolution image data from a 3D pre-scan, and FIG. 5 represents a coronal view of higher resolution volumetric image data from the corresponding volumetric scan.

In one instance, the combiner 127 registers the 3D pre-scan image data to the volumetric image data. Rigid and/or elastic registration algorithms can be used. As described herein, registering the 3D pre-scan and volumetric image data facilitates mitigating motion of the scanned subject between the 3D pre-scan and the volumetric scan. In another instance, the combiner 127 only fuses the 3D pre-scan image data to the volumetric image data, as the 3D pre-scan and volumetric scan are acquired in the same coordinate system and thus, the 3D pre-scan image data to the volumetric image data are already approximately registered.

An example of a result of the combining is shown in FIG. 19, which shows combined image data 1902, which includes volumetric image data 1904 and 3D pre-scan image data 1906.

Returning to FIG. 18, the segmentor 128 includes a segmentation processor 1914 that segments tissue of interest from the volumetric image data 1904 based on the volumetric image data and/or based on the combined image data 1902. The tissue of interest can be identified through a signal from the console 114 (FIG. 1) indicating a user identified tissue of interest, from the volumetric image data (e.g., an entry in a header of the electronic data indicating a type of scan, for example, cardiac scan would indicate the heart is the tissue of interest), and/or otherwise.

The segmentation processor 1914 segments the tissue of interest using at least two different segmentation algorithms. In the illustrated embodiment, at least two different segmentation algorithms include: a higher resolution segmentation algorithm 1910 and a lower resolution segmentation algorithm 1912. The segmentation processor 1914 employs the higher resolution segmentation algorithm 1910 to segment the higher resolution volumetric image data 1904 and the lower resolution segmentation algorithm 1912 to segment the lower resolution 3D pre-scan image data. The delineation between higher and lower resolution image data (i.e., voxels or pixels) in the registered image data 1902 is known from the registration.

In a variation, a same segmentation algorithm is used to segment both the higher resolution volumetric image data 1904 and the lower resolution. In yet another instance, the combined image data 1902 is generated based on more than two image data sets, for example, the volumetric image data 1904, the 3D pre-scan image data 1906, and one or more other sets of 3D pre-scan image data. In this instance, the segmentor 128 can employ a different resolution segmentation algorithm for each data set, a same resolution segmentation algorithm for at least two of the sets of 3D pre-scan image data, and/or a same resolution segmentation algorithm for all of the sets of image data.

In one non-limiting instance, the output of the segmentation processor 1914 includes the combined image data 1902 with the tissue of interest delineated therein. The delineation can be through visual graphical indicia such as a line following the perimeter of the tissue of interest, with the line in black and white or color. In another non-limiting instance, the output of the segmentor 128 includes just the tissue of interest, with the remaining image data discarded or masked.

The output of the segmentor 128 includes the segmented volumetric image data. The segmented volumetric image data can be displayed via the console 114, stored in the image data storage 120 (FIG. 1), conveyed to another device, and/or otherwise processed.

In one non-limiting instance, the 3D pre-scan image data is not displayed with the volumetric image data or the segmented volumetric image data. As such, the user sees the output as in a configuration in which the 3D pre-scan image data is not used for the segmentation; that is, only the segmented volumetric image data. However, segmentation is performed on the larger combined image data 1902, which includes more of the tissue of interest and/or additional anatomical structure, both of which can be used to provide a more accurate segmentation, relative to a configuration in which the 3D pre-scan image data is not used as described herein.

By way of non-limiting example, for a relatively small volume scan performed to measure airway wall thickness to rule out COPD, where the extent of the scan covers the airway wall plus a margin, the 3D pre-scan image data provides additional airway data, which can be used to help distinguish airways from lung parenchyma. Generally, the extent of the scan is limited to the airway wall plus a margin to limit the dose deposited to the subject.

In an another example, where the entire heart is scanned in a scan that covers the heart plus a margin, the 3D pre-scan image data provides image data of tissue surrounding the heart. Likewise, the extent of the full organ scan is limited to the full organ plus a margin to limit the dose deposited to the subject. Where the additional image data includes the liver and the boundary between the heart and the liver is unclear, simultaneous segmentation of the liver and the heart may improve delineation of the heart with respect to the liver.

In a variation, the 3D pre-scan image data can also be displayed. The segmented volumetric image data and 3D pre-scan image data can be individually or concurrently displayed, for example, side by side, or one superimposed over the other. In another variation, the combined image data 1902 is also displayed. Likewise, the combined image data 1902 can be displayed by itself or concurrently along with the segmented volumetric image data and/or the 3D pre-scan image data.

FIG. 20 illustrates a method for segmenting a region of interest from volumetric image data based on combining the volumetric image data with the 3D pre-scan data used to plan the volume scan.

It is to be appreciated that the ordering of the acts of these methods is not limiting. As such, other orderings are contemplated herein. In addition, one or more acts may be omitted and/or one or more additional acts may be included.

At 2002, a 3D pre-scan is performed, generating 3D pre-scan image data.

At 2004, a volume scan plan is created based on the 3D pre-scan image data.

At 2006, a volume scan is performed, based on the volume scan plan, generating volumetric image data.

At 2008, the 3D pre-scan image data is combined with the volumetric image data, generating combined image data.

At 2010, tissue of interest is segmented from the volumetric image data using the combined image data, generating segmented combined image data, as disclosed herein and/or otherwise.

At 2012, the segmented volumetric image data component is visually displayed.

The above acts may be implemented by way of computer readable instructions, encoded or embedded on computer readable storage medium, which, when executed by a computer processor cause the processor to carry out the described acts. Additionally or alternatively, at least one of the computer readable instructions is carried by a signal, carrier wave and other transitory medium and implemented by the computer processor.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   determining a registration transform between first three dimensional pre-scan image data and second three dimensional pre-scan image data based on a predetermined registration algorithm; and
   registering first volumetric scan image data and second volumetric scan image data based on the registration transform, generating registered image data,
   wherein a field of view of the first volumetric scan image data is less than a field of view of the first three dimensional pre-scan image data, and a field of view of the second volumetric scan image data is less than a field of view of the second three dimensional pre-scan image data.

2. The method of claim 1, wherein the first volumetric scan image data is acquired with a first scan plan determined based on the first three dimensional pre-scan image data, and the second volumetric scan image data is acquired with a second scan plan determined based on the second three dimensional pre-scan image data.

3. The method of claim 1, wherein the first three dimensional pre-scan image data and the second three dimensional pre-scan image data are acquired with a lower patient dose than the first volumetric scan image data and the second volumetric scan image data.

4. The method of claim 1, wherein the first three dimensional pre-scan image data and the second three dimensional pre-scan image data have a lower image quality than the first volumetric scan image data and the second volumetric scan image data.

5. The method of claim 2, further comprising:
determining the first scan plan by identifying a first scan start location and a first scan end location in the first three dimensional pre-scan image data;
performing the first scan plan, thereby generating the first volumetric scan image data;
determining the second scan plan by identifying a second scan start location and a second scan end location in the second three dimensional pre-scan image data; and
performing the second scan plan, thereby generating the second volumetric scan image data.

6. The method of claim 1, wherein a field of view of the first volumetric scan image data is a sub-set of a field of view of the first three dimensional pre-scan image data, and a field of view of the second volumetric scan image data is a sub-set of a field of view of the second three dimensional pre-scan image data.

7. The method of claim 1, wherein the field of view of the first volumetric scan image data and the field of view of the second volumetric scan image data are not a same field of view.

8. The method of claim 7, further comprising:
adding a sub-portion of the first three dimensional pre-scan image data to the first volumetric scan image data and a sub-portion of the second three dimensional pre-scan image data to the second volumetric scan image data, creating extended first volumetric scan image data and extended second volumetric scan image data.

9. The method of claim 8, wherein the extended first volumetric scan image data and the extended second volumetric scan image data have a same extended field of view.

10. The method of claim 8, further comprising:
registering the extended first volumetric scan image data and the extended second volumetric scan image data based on the registration transform, generating the registered image data.

11. The method of claim 1, wherein the first three dimensional pre-scan image data and the second three dimensional pre-scan image data are acquired at a first motion state and the first volumetric scan image data and the second volumetric scan image data are acquired at a second, different motion state, and further comprising:
determining a first motion vector field for the first volumetric scan image data based on the first volumetric scan image data and the first three dimensional pre-scan image data;
determining a second motion vector field for the second volumetric scan image data based on the second volumetric scan image data and second three dimensional pre-scan image data;
motion compensating the first volumetric scan image data based on the first motion vector;
motion compensating the second volumetric scan image data based on the second motion vector; and
registering the motion compensated first volumetric scan image data and the motion compensated second volumetric scan image data based on the registration transform, generating the registered image data.

12. The method of claim 11, wherein the first motion state is respiratory inhale and the second motion state is respiratory exhale or vice-versa.

13. The method of claim 11, further comprising:
employing the first motion vector field to modify a general motion model, thereby creating a first subject-specific motion model;
employing the second motion vector field to modify the general motion model, thereby creating a second subject-specific motion model;
motion compensating the first volumetric scan image data based on the first subject-specific motion model;
motion compensating the second volumetric scan image data based on the second subject-specific motion model; and
registering the motion compensated first volumetric scan image data and the motion compensated second volumetric scan image data based on the registration transform, generating the registered image data.

14. A system, comprising:
a processor, including:
a pre-scan registerer that determines a registration transform between first three dimensional pre-scan image data and second three dimensional pre-scan image data based on a predetermined registration algorithm;
determining a first motion vector field for first volumetric scan image data based on the first volumetric scan image data and the first three dimensional pre-scan image data; and
motion compensating the first volumetric scan image data based on the first motion vector field; and
a volume registerer that registers the motion compensated first volumetric scan image data and second volumetric scan image data based on the registration transform, generating registered image data.

15. The system of claim 14, wherein the first volumetric scan image data is acquired with a first scan plan determined based on the first three dimensional pre-scan image data, and the second volumetric scan image data is acquired with a second scan plan determined based on the second three dimensional pre-scan image data.

16. The system of claim 14, wherein the first three dimensional pre-scan image data and the second three dimensional pre-scan image data are acquired with a lower patient dose than the first volumetric scan image data and the second volumetric scan image data.

17. The system of claim 14, wherein a field of view of the first volumetric scan image data and a field of view of the second volumetric scan image data are not a same field of view, and the processor further comprising:
a field of view combiner that combines the field of view of the first volumetric scan image data and the field of view of the second volumetric scan image data, producing a combined field of view of the first and the second volumetric scan image data, wherein the combined field of view is greater than either of the field of view of the first volumetric scan image data and the field of view of the second volumetric scan image data;
a missing image data identifier that identifies a first sub-portion of the combined field of view that is not part of the field of view of the first volumetric scan image data and a second sub-portion of the combined field of view that is not part of the field of view of the second volumetric scan image data;
an image data extractor that extracts the identified first and second sub-portions respectively in the first three dimensional pre-scan image data and the second three dimensional pre-scan image data; and
an image data extender that extends the first volumetric scan image data with the extracted identified first sub-portion and that extends the second volumetric scan image data with the extracted identified second sub-portion.

18. The system of claim 14, wherein the second three dimensional pre-scan image data is acquired at the first motion state and the second volumetric scan image data is acquired at the second, different motion state, and the processor further comprising:

determining a second motion vector field for the second volumetric scan image data based on the second volumetric scan image data and second three dimensional pre-scan image data;

motion compensating the second volumetric scan image data based on the second motion vector field; and registering the motion compensated first volumetric scan image data and the motion compensated second volumetric scan image data based on the registration transform, generating the registered image data.

19. A method, comprising:

combining 3D pre-scan image data with volumetric image data from a volume scan, wherein the 3D pre-scan image data was used to plan the volume scan, generating combined image data;

segmenting tissue of interest from the volumetric image data based on the combined image data; and visually displaying the segmented volumetric image data.

20. The method of claim 19, wherein the 3D pre-scan image data has a first image contrast resolution and the volumetric image data has a second image contrast resolution, and the first image contrast resolution is lower than the second image contrast resolution.

21. The method of claim 19, further comprising:

segmenting a volumetric image data sub-portion of the combined image data using a higher resolution segmentation algorithm; and segmenting a 3D pre-scan image data sub-portion of the combined image data using a lower resolution segmentation algorithm.

22. The method of claim 21, wherein the segmenting includes combining the organ and combining the sub-portion of the at least one neighboring organ.

23. The method of claim 19, wherein the tissue of interest is an organ, the volumetric image data includes the entire organ, and the 3D pre-scan image data includes at least a sub-portion of at least one neighboring organ.

24. A system, comprising:

a processor, including:

a combiner that combines 3D pre-scan image data with volumetric image data from a volume scan, wherein the 3D pre-scan image data was used to plan the volume scan, generating combined image data; and a segmentor that segments tissue of interest from the volumetric image data based on the combined image data, wherein the 3D pre-scan image data has a first image contrast resolution and the volumetric image data has a second image contrast resolution, and the first image contrast resolution is lower than the second image contrast resolution.

25. The system of claim 24, wherein the segmentor segments a volumetric image data sub-portion of the combined image data using a higher resolution segmentation algorithm and segments a 3D pre-scan image data sub-portion of the combined image data using a lower resolution segmentation algorithm.

26. The system of claim 24, wherein the tissue of interest is an organ, the volumetric image data includes the entire organ, and the 3D pre-scan image data includes at least a sub-portion of at least one neighboring organ.

27. The system of claim 24, wherein the segmentor segments the organ and segments the sub-portion of at least one neighboring organ.

* * * * *